(12) United States Patent  
Müller-Paul (10) Patent No.: US 8,714,409 B2
(45) Date of Patent: May 6, 2014

(54) DISPENSING CARTRIDGE (75) Inventor: Dirk Müller-Paul, München (DE)

(73) Assignee: 3M Innovative Properties Company, St. Paul, MN (US)

( * ) Notice: Subject to any disclaimer, the term of this patent is extended or adjusted under 35 U.S.C. 154(b) by 1965 days.

(21) Appl. No.: 11/566,830

(22) Filed: Dec. 5, 2006

(65) Prior Publication Data

US 2007/0158362 A1 Jul. 12, 2007

(30) Foreign Application Priority Data

Dec. 6, 2005 (EP) .................................. 05026606

(51) Int. Cl.
B67D 7/70 (2010.01)

(52) U.S. Cl.
USPC ......... 222/137; 222/145.6; 222/327; 222/475

(58) Field of Classification Search
USPC .............. 222/137, 325, 145.6, 327, 467, 475, 222/475.1; 433/80, 82; 16/425, 406, 422, 16/418, 419, 420, 411, 110.1
See application file for complete search history.

(56) References Cited

U.S. PATENT DOCUMENTS

| 2,252,054 | A | * | 8/1941 | Welch | 43/23 |
| 2,634,888 | A | | 4/1953 | Sherbondy | 222/327 |
| 3,231,138 | A | * | 1/1966 | Serafini | 222/475 |
| 3,820,511 | A | * | 6/1974 | Katzakian | 222/475 |
| 4,615,469 | A | | 10/1986 | Kishi et al. | 222/327 |
| 4,827,566 | A | * | 5/1989 | Richins | 16/422 |
| 5,005,735 | A | | 4/1991 | Keller | 222/137 |
| 5,184,757 | A | | 2/1993 | Giannuzzi | 222/82 |
| RE34,487 | E | | 12/1993 | Keller | 222/137 |
| 5,271,527 | A | * | 12/1993 | Haber et al. | 222/43 |
| 5,513,780 | A | * | 5/1996 | Buono | 222/475 |
| 5,779,675 | A | * | 7/1998 | Reilly et al. | 604/131 |
| 5,875,928 | A | * | 3/1999 | Muller et al. | 222/82 |
| 6,030,214 | A | * | 2/2000 | Zwingenberger | 433/82 |
| 6,048,201 | A | | 4/2000 | Zwingenberger | 433/90 |
| 6,311,869 | B1 | | 11/2001 | Hörth et al. | 222/137 |
| 2003/0014835 | A1 | * | 1/2003 | Dimig et al. | 16/110.1 |

FOREIGN PATENT DOCUMENTS

| DE | 34 18 052 C2 | 12/1984 | B05C 17/00 |
| DE | 100 38 882 A1 | 4/2001 | A61C 9/00 |
| EP | 0 291 753 B1 | 11/1988 | B05C 17/00 |
| EP | 0 910 995 A2 | 4/1999 | A61C 5/06 |
| EP | 1 044 727 A2 | 10/2000 | B05C 17/01 |
| EP | 1044727 A2 * | 10/2000 | |
| EP | 1 602 342 A1 | 12/2005 | A61C 5/06 |
| WO | WO 97/18145 | 5/1997 | B65D 81/32 |

* cited by examiner

*Primary Examiner* — Daniel R Shearer (57) ABSTRACT

A dispensing cartridge, particularly for dental impression materials, comprises a locking member for locking a tip to the dispensing cartridge and/or to a container accommodated in the dispensing cartridge. The locking member has a first end and a second end, and is pivotally connectable with the dispensing cartridge at the first end. The second end of the locking member is adapted for releasable locking engagement with the tip. Furthermore, the locking member comprises a first portion that provides a grasping feature for the user for manipulating the dispensing cartridge at the locking member.

2 Claims, 6 Drawing Sheets

DISPENSING CARTRIDGE

This application claims priority from European Application No. 05026606.3, filed Dec. 6, 2005.

FIELD OF THE INVENTION

The present invention relates to a dispensing cartridge, particularly for dental impression materials, of the type adapted to be releaseably received in an applicator unit having a moveable plunger.

BACKGROUND OF THE INVENTION

A number of dispensing devices are available for dispensing various types of materials. In many instances, the dispensing device is an assembly that includes a reusable dispenser or applicator and a disposable cartridge. The cartridge typically comprises one or more compartments. Container, such as foil bags, containing the material to be dispensed are accommodated in the compartments of the cartridge. The cartridge contains a quantity of a material to be dispensed and is releaseably received in a receptacle or chamber of the applicator.

In one type of dispensing devices, that include an applicator and a cartridge, the applicator has a plunger that is advanced by the user during a dispensing operation. Often, the plunger is positioned at an open end of the cartridge and bears against a piston within the cartridge. As the plunger is advanced to move the piston, the piston expels a quantity of material through a front outlet opening of the cartridge, where it may be mixed with material expelled from another cartridge, or used by itself. Dispensing devices with cartridges are often used in the field of dentistry for mixing and dispensing dental compositions of two components, such as impression materials, restoratives, adhesives, cements, etching gels, sealants and the like. The dispensing cartridge of such devices is made from a plastic material and comprises two compartments formed by two cylindrical bodies arranged in parallel to each other. Each compartment contains a specific component, usually a base paste or a catalyst paste, each contained within its own container, such as a foil or plastic bag. These two components are pressed from their respective foil bags out into a mixing tip where the required dental material is prepared. The pressure further urges the mixture out of the mixing tip so that the dental professional can use it as desired.

One type of such dispensing devices is an assembly (e.g., the Garant™ dispenser available from 3M ESPE AG) that includes a reusable, hand-operated applicator and a disposable cartridge (e.g., the cartridge for the polyether impression material Permadyne™ Garant™ available from 3M ESPE AG). The two compartments are of the same cylindrical shape and size and are pre-filled with the two components to be mixed and dispensed.

Another type of such dispensing devices is an automatic dispensing system (e.g., Pentamix™ available from 3M ESPE AG) that includes a motor-driven mixing or applicator unit and reusable and interchangeable cartridges (e.g., the cartridge for the polyether impression material Impregum™ Penta™ H DuoSoft, or the cartridge for the polyether impression material Permadyne™ Penta™, or the cartridge for the vinyl polysiloxane impression material Express™ Penta™ H, all available from 3M ESPE AG). The applicator unit comprises a space that receives the cartridge, and a cover that closes the space once the cartridge is placed in the dispensing device. The two cylindrical compartments of the cartridge have different diameters, and, in use, each accommodates a disposable foil bag pre-filled with the respective component. The larger compartment accommodates the foil bag with the base paste. The smaller compartment accommodates the foil bag with the catalyst paste. The mixing or applicator unit comprises a chamber for holding the cartridge and two parallel motor-driven plungers designed to plunge into the respective compartments and to exert pressure on the components contained in the foil bags. Both foil bags comprise a respective cap that fits onto the rim of the respective cylindrical body of the dispensing cartridge. A pivotable lever is used for locking the mixing tip so that it does not fall off of the caps of the foil bags when pressure is applied by the plungers.

Figure 1:
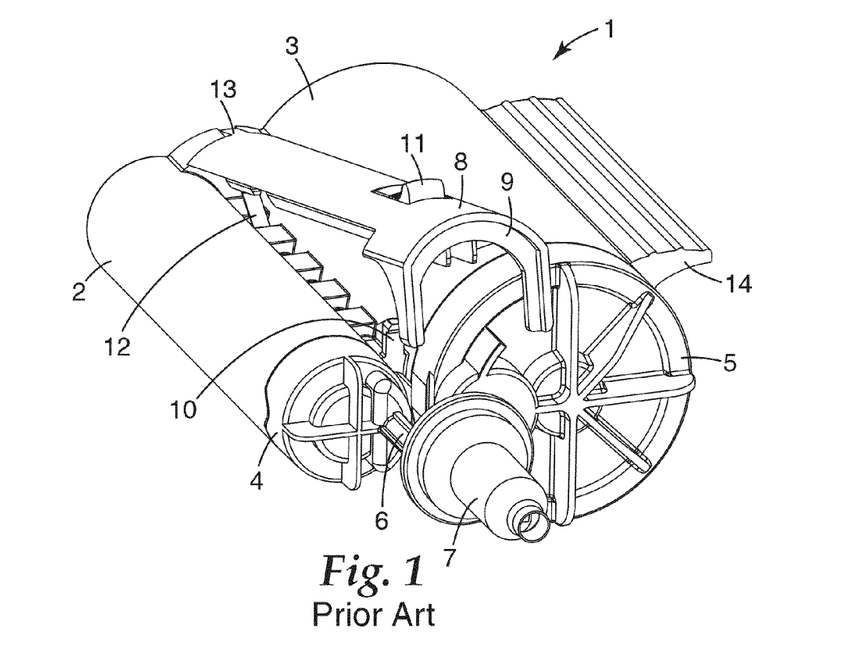
FIG. 1 is a front perspective view of a conventional dispensing cartridge.

FIG. 1 shows such a conventional cartridge 1 having two parallel cylindrical compartments 2, 3 with different diameters. In FIG. 1, each compartment already accommodates a foil bag comprising respective caps 4, 5. Each cap comprises an outlet tube (in FIG. 1, only the outlet tube 6 of cap 4 is shown), and adjacent to these outlet tubes is a mixing tip 7. A lever 8 that extends along the longitudinal axis of the cartridge is pivotally hinged to the cartridge at its rear end. At the front end of the lever 8, the lever comprises an essentially U-shaped locking member 9, comprising two locking arms that engage corresponding locking surfaces or flanges of the mixing tip 7. This positions the mixing tip properly relative to the outlet tubes 6 of the caps.

Figure 2:
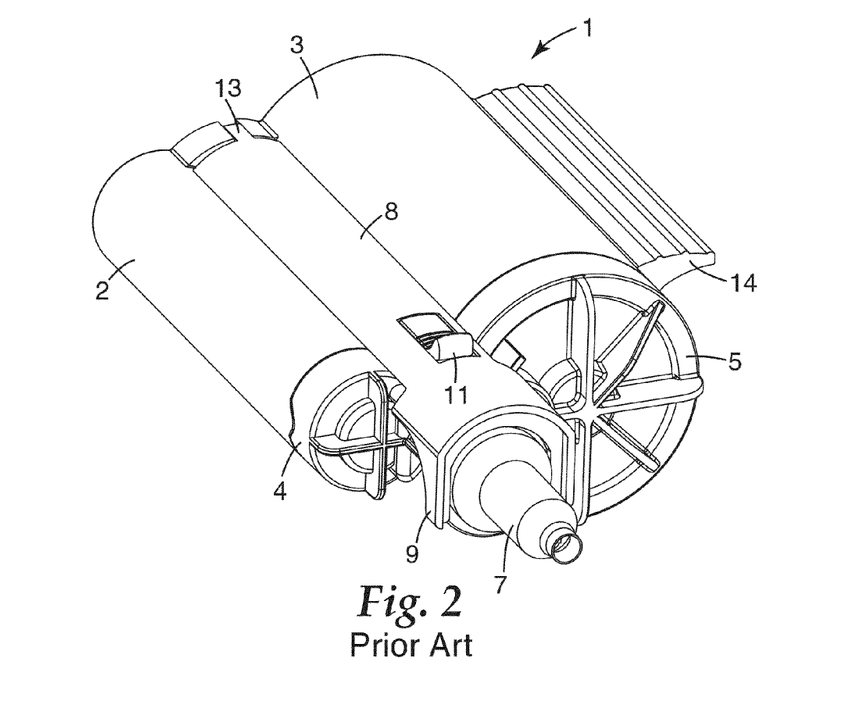
FIG. 2 is a front perspective view of the conventional dispensing cartridge of FIG. 1 with the locking lever in its engaged position.

FIG. 2 shows the cartridge 1 with the lever 8 in its fully engaged position. Due to the two locking arms engaging a circumferential flange at the rear end of the mixing tip 7, the mixing tip 7 is held tight against the outlet tubes 6 of the foil bag caps 4, 5. In order to hold the lever 8 in its engaged state, an engagement mechanism 10 is provided which engages a corresponding surface at the underside of the lever 8. This engagement mechanism 10 can be released by means of a release slide 11. In order to facilitate a quick release of the lever 8 from mixing tip 7, a leaf spring 12 is provided adjacent to the lever hinge 13. Once the engagement mechanism 10 is released with the release slide 11, lever 8 springs upwards and away from the mixing tip 7 due to the bias force of the leaf spring 12.

FIGS. 1 and 2 also show a handle 14 that is provided at one side of the cartridge, specifically on the side of the larger diameter compartment 3. With this handle 14, the cartridge 1 can be picked up and removed from the applicator unit, for example, so that the foil bags can easily be changed. However, since the handle 14 is provided at a side of the cartridge 1 like a wing, removal of the entire cartridge 1 from the mixing unit might be inconvenient to the user.

EP 1 044 727 A2 relates to a device for mixing and dispensing of a viscous liquid consisting of at least two components via two pistons. The liquid components are held in containers that are part of an insert and connected to a mixer. The pistons are arranged in a housing of the device and act upon such containers. The insert is accommodated in a cartridge that is part of a housing attachment. The cartridge is rotatably connected with the housing attachment so that it is rotatable between an operating position and an open position, wherein the insert can be removed from or inserted into the cartridge in the open position, and the insert can be secured in the cartridge in the operating position.

U.S. Pat. No. 5,184,757 generally relates to gun-type dispensers for discharging a viscous fluid or paste, such as a sealing or bonding agent, from a container storing this agent. The gun includes a pair of cylindrical barrels for accommodating sealed foil packs having stored therein two components to be extruded and intermixed. Fitting into the leading ends of barrels and are end caps and of a mixing manifold. The manifold, which is removable from the barrel, is locked in place by a swing gate having a pair of parallel arms whose rear ends are pivotally connected to opposite sides of a stock piece. Secured to the front ends of these arms is a gate which when the gate is lowered engages the exposed faces of caps. When the swing gate is thereafter raised, one may then withdraw the manifold from the barrels.

U.S. Pat. No. 2,634,888 relates to a dispensing gun with means for inserting removable containers. The apparatus described in U.S. Pat. No. 2,634,888 comprises essentially a handle carrying a manual mechanism for expelling the contents the cartridge and having means for positioning the rear end of the cartridge; a cup-like member to engage the front end of the cartridge and an extensible connecting device between said front engager and the handle whereby the cartridge may be effectively clamped in the apparatus to constitute the barrel of the gun or be released therefrom when empty. The clamping mechanism comprises a pair of frame bars extending parallel with each other on opposite sides of the cartridge, and have sliding or telescoping engagement with a pair of side bars which are secured to the front abutment. An operating lever is pivotably linked to the frame bars, and the operating lever and suitable linkage connects with the bars in a manner to spread them or contract them. With such arrangement, which is shown in FIG. 2 of U.S. Pat. No. 2,634,888 for example, a pivotal or rotational movement of the operating lever is translated into a translational movement of the frame bars and side bars relative to each other in order to clamp the cartridge in the apparatus.

EP-A-1 602 342 (document under Art. 54(3) EPC) relates to a dispensing cartridge having a locking assembly for locking a tip in position relative to at least one compartment. The locking assembly comprises a first movable member comprising a first end and a second movable member comprising a first end and a second end. The second end of the second movable member is adapted for releasable locking engagement with the tip. The first movable member is operationally connected to the second movable member such that a movement of the first end of the first movable member is transmitted to the first end of the second movable member causing the second movable member to also move. Movement of the first end of the first movable member in a first direction causes the second end of the second movable member to release the tip, and movement of the first end of the first movable member in a second direction causes the second end of the second movable member to engage the tip. The first movable member may form part of a handle.

Further reference is made to EP-A-0 291 753, EP-A-0 910 995, WO 97/18145, DE-A-100 38 882, and DE-A-34 18 052.

SUMMARY OF THE INVENTION

According to a first aspect, the invention provides a dispensing cartridge, particularly for dental impression materials, comprising a locking member for locking, for example a tip to the dispensing cartridge and/or to a container accommodated in the dispensing cartridge. The locking member has a first end and a second end, and is pivotally connectable with the dispensing cartridge at the first end. The second end of the locking member is adapted for releasable locking engagement, for example with the tip. Furthermore, the locking member comprises a first portion that provides a grip for the user to manipulate the dispensing cartridge. Preferably, the grip of the locking member allows grasping of the dispensing cartridge and insertion into or removal from an applicator unit while the locking member is in locking engagement with the tip.

In the context of the present invention, the term "locking" means that slight movement is permitted so long as it does not interfere with the function of the dispensing cartridge.

It is preferred that the dispensing cartridge of the invention comprises a one-piece locking member.

The locking member is preferably elongated, and, for example, forms a lever arm. In the locking position of the locking member, the locking member preferably extends along the longitudinal axis of the dispensing cartridge.

The first portion of the locking member providing a grip is preferably is located in the area of the first end of the locking member.

According to a first preferred embodiment of the dispensing cartridge of the invention, the first portion of the locking member is raised relative to the dispensing cartridge to provide a handle for the user. The raised first portion preferably has a first section and a second section extending upwards from the locking member surface. The first section and the second section are preferably spaced from each other and connected by a third section. More preferably, the first, second, and third sections form an inverse U. Alternatively, the first, second, and third sections form a convex-shaped raised portion. In this embodiment, the first section is preferably adjacent to the first end of the locking member, whereas the second section is spaced from the first section in longitudinal direction of the locking member. As an option, the raised portion extends along substantially the whole length of the locking member.

According to a second preferred embodiment of the dispensing cartridge of the invention, the grip consists of a rib extending from the surface of the locking member. According to the present invention, the term "rib" means an essentially closed surface that can be grasped by applying pressure from both sides. The rib preferably extends upwards from the surface of locking member, where the term "upwards" is relative to a state in which the locking member engages the tip and is substantially horizontally oriented. Preferably, the rib extends along the longitudinal axis of the locking member. Alternatively, the rib extends across the longitudinal axis of the locking member. In this case, the rib preferably is in the form of an inverse U thus providing a through hole between the surface of the locking member and the U.

In a dispensing cartridge according to a third embodiment of the invention, the grip consists of at least one through hole through the first portion of the locking member. The at least one through hole is preferably sized such that a user's finger is insertable through the hole.

It is preferred according to all embodiments of the invention that the locking member is removably connectable to the dispensing cartridge.

The dispensing cartridge of the invention is used with dispensing devices such as the above-described Pentamix™ automatic dispensing system. In this case, the cover of the dispensing device may eventually comprise a recess to accommodate the handle of the locking member of the invention.

In the present dispensing cartridge, the at least one compartment comprises a body having an open end for receiving a plunger of an applicator, and having an outlet opening. The at least one compartment extends between the open end and outlet opening.

The dispensing cartridge of the present inventions preferably contains a first compartment (preferably adapted for receiving a first container) comprising a base material and a second compartment (preferably adapted for receiving a second container) comprising a catalyst material that together form a dental impression material after having been mixed.

Preferably, the dental impression material is a polyether impression material or polysiloxane impression material. The containers are preferably foil bags each closed by a cap, each of which comprises an outlet tube. The locking member preferably comprises at least one engagement element for engaging such cap(s) of the container.

The locking member is preferably adapted for locking the tip to the at least one container. For example, the second end of the locking member comprises engagement surfaces that are engageable with a complementary engagement surface at the tip. In more detail, the second end of the locking member is preferably substantially U-shaped, and the two legs of the U are engageable with a corresponding flange at the rear end of the tip.

It is also preferred that the dispensing cartridge comprises a release mechanism for releasing the locking engagement of the locking member with the tip. In the preferred embodiment of a one-piece locking member, the term "one-piece" does not encompass the release mechanism.

The tip usable with a dispensing cartridge according to the invention is preferably a dispensing tip or a mixing tip.

According to a second aspect, the present invention provides a kit comprising an applicator unit comprising at least one plunger and at least one dispensing cartridge according to the invention. The invention also provides a kit comprising a dispensing cartridge according to the invention comprising a paste, and a tip.

According to a further aspect of the invention, the grip for the user is extended from, and retractable into, the locking member. Thus, the grip is retractable into the cartridge assembly when not in use, but can be pulled upward when needed to function as a handle. This arrangement is advantageous because it saves space in the closed applicator unit. As an example, the retractable handle is spring-loaded so that when the top of the applicator unit is opened, the handle springs upward, but when the top is closed the handle is pressed downward, again saving space.

BRIEF DESCRIPTION OF THE DRAWINGS

Preferred embodiments of the invention are described in more detail below with reference to the attached drawings, which are by way of example only.

DETAILED DESCRIPTION OF PREFERRED EMBODIMENTS

Figure 3:
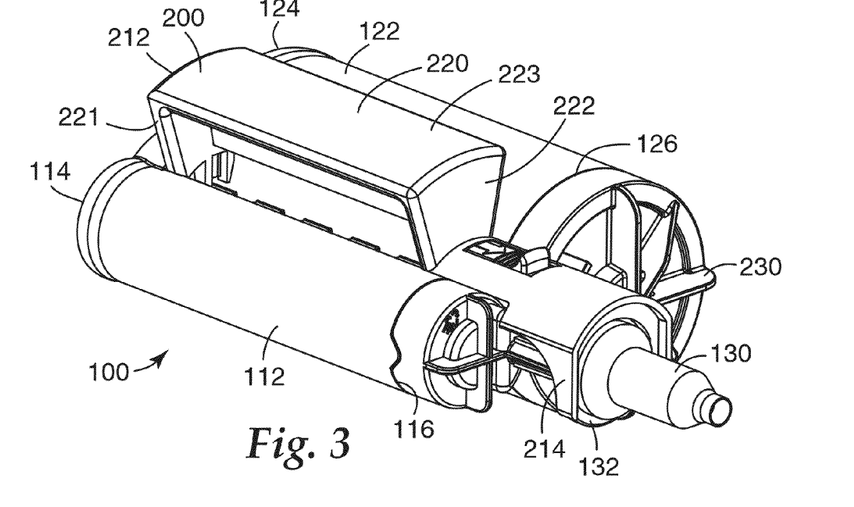
FIG. 3 is a front perspective view of the dispensing cartridge according to one embodiment of the invention with the locking member in its open position.
Figure 4:
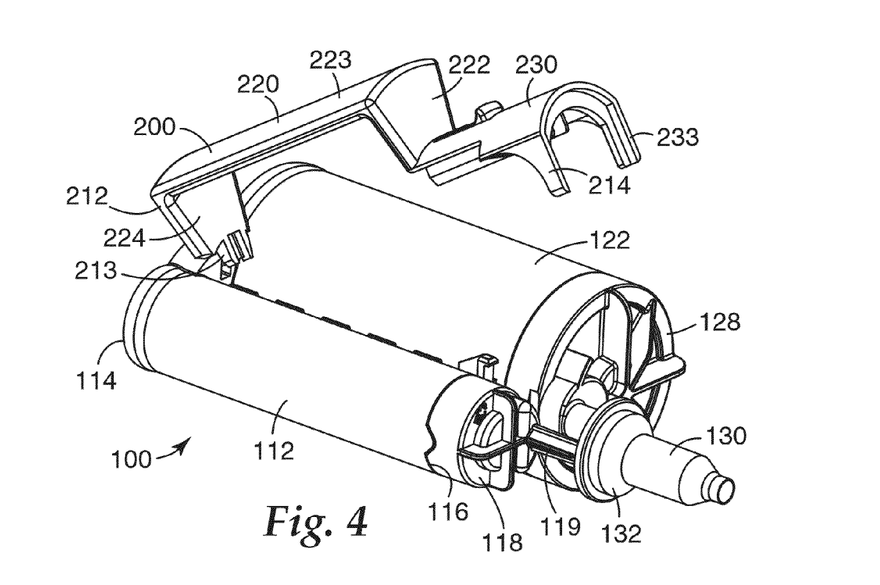
FIG. 4 is a front perspective view of dispensing cartridge of FIG. 3 with the locking member in its engaged position.

An example of a dispensing cartridge of a first embodiment of the invention is illustrated in FIGS. 3 and 4, and is designated by reference numeral 100. The cartridge 100 according to this embodiment comprises a first compartment with a body 112. Specifically, the body 112 includes a rear open end 114 and a front outlet opening 116 that is spaced from the open end 114. The compartment is elongated and extends from the rear open end 114 to the outlet opening 116.

The dispensing cartridge as shown in the Figures comprises a second compartment having a body 122. The body 122 includes a rear open end 124 and a front outlet opening 126 that is remote from the open end 124. The second compartment is elongated and extends from the open end 124 to the outlet opening 126.

In the illustrated embodiment, the dispensing cartridge 100 comprises a locking member 200 in the form of a pivotable lever arm that is connected at its rear end to the dispensing cartridge 100. Locking member 200 is connected at its first end 212 to the remainder of the dispensing cartridge by a hinge 213. Due to this connection, locking member 200 is rotatable about hinge 213 and can be angularly displaced as shown, e.g., in FIG. 4. In particular, locking member 200 is shown in FIG. 4 in its non-engaged position, and is rotatable downwards, towards the two compartments of the dispensing cartridge 100. In order to allow a defined non-engaged position of locking member 200 as shown in FIG. 4, a bias function, provided by for example a bias member like a coil spring, may be provided.

The locking member 200 further comprises at its second end 214 a second portion that is substantially L-shaped. The second portion 230 comprises engagement surfaces for releasable engagement with corresponding engagement surfaces 132, for example, an annular flange, of the mixing tip 130. The second portion 230 is preferably U-shaped, as is best seen in FIG. 4. The two legs 233 and 234 of the U are formed such that they correspond to the annular engagement flange 132 of the mixing tip 130. In the engaged position of the locking member 200, i.e. in the locking position of the second portion 230 as shown in FIG. 3, the legs 233, 234 engage the engagement flange 132 of mixing tip 130 which prevents the mixing tip from being removed from the dispensing cartridge or from being pressed off of the dispensing cartridge due to the pressure applied by the pistons to the containers by the applicator unit. As shown in FIG. 4, the mixing tip 130 is connected to outlet tubes 119 of the caps 118, 128 of the containers, which are, for example, foil bags containing the material to be dispensed.

Figure 5:
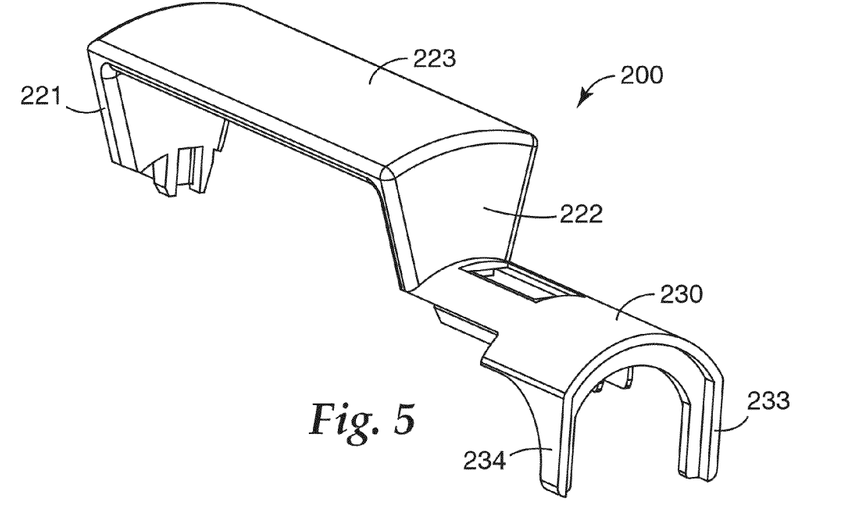
FIG. 5 is a front perspective view of the locking member of the dispensing cartridge of FIGS. 3 and 4.

In the preferred embodiment shown in FIGS. 3 to 5, the grasping feature that enables the user to grasp the dispensing cartridge at the locking member is provided in the form of a portion of the locking member that is raised relative to the dispensing cartridge. The raised portion 220 of the locking member 200, in the example shown in FIGS. 3 to 5, comprises a first extending section 221 at the rear or first end of the locking member 200, and a second extending section 222 closer to the second end 214 of the locking member 200. These two sections 221 and 222 are connected by a third section 223. Third section 223 extends substantially parallel to the remainder of the locking member 200 so that the two sections 221, 222, and the third section 223 provide a structure in the form of an inverse U.

Figure 6:
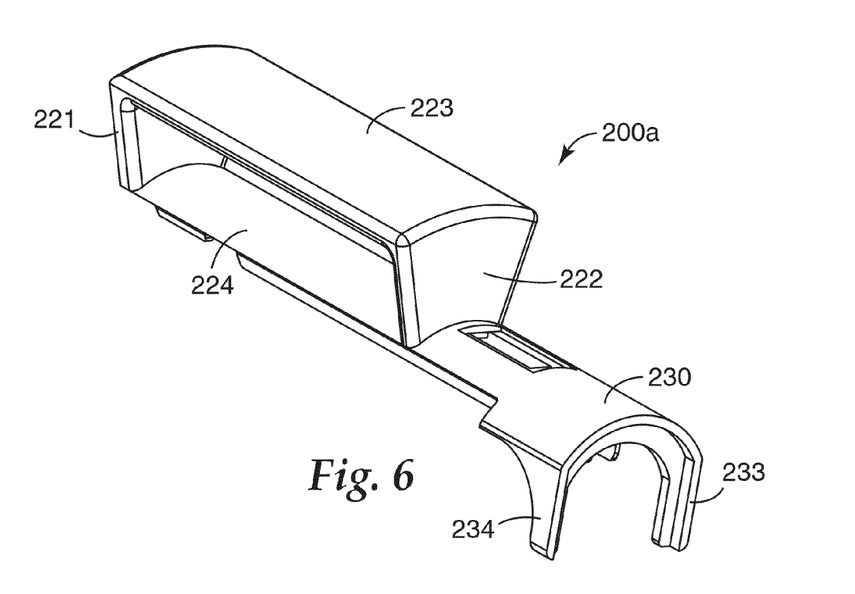
FIG. 6 is a front perspective view of an alternative locking member shown in FIG. 6.

As shown in FIGS. 4 and 5, the first upstanding section 221 terminates in third section 223, which, in turn, terminates in second extending section 222. Second extending section 222 then terminates into second portion 230 of the locking member 200. An alternative to this design is shown in FIG. 6. Here, locking member 200a is formed like the locking member 200 shown in FIG. 5, but additionally comprises a fourth section 224 extending between the lower ends of the two extending sections 221, 222. This section could add structural strength and stability to the locking member.

Figure 7:
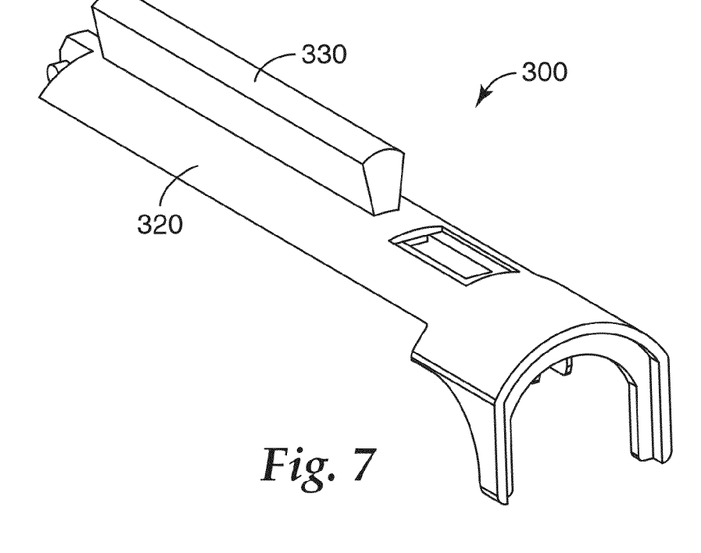
FIG. 7 is a front perspective view of an alternative locking member according to a further embodiment of the invention.

FIG. 7 shows an alternative embodiment of the invention. Locking member 300 shown in FIG. 7 comprises a rib 330 that extends from first portion 320. In the embodiment shown in FIG. 7, the rib extends along the longitudinal axis of the locking member 300, and provides another manner for a user to grasp the cartridge.

Figure 8:
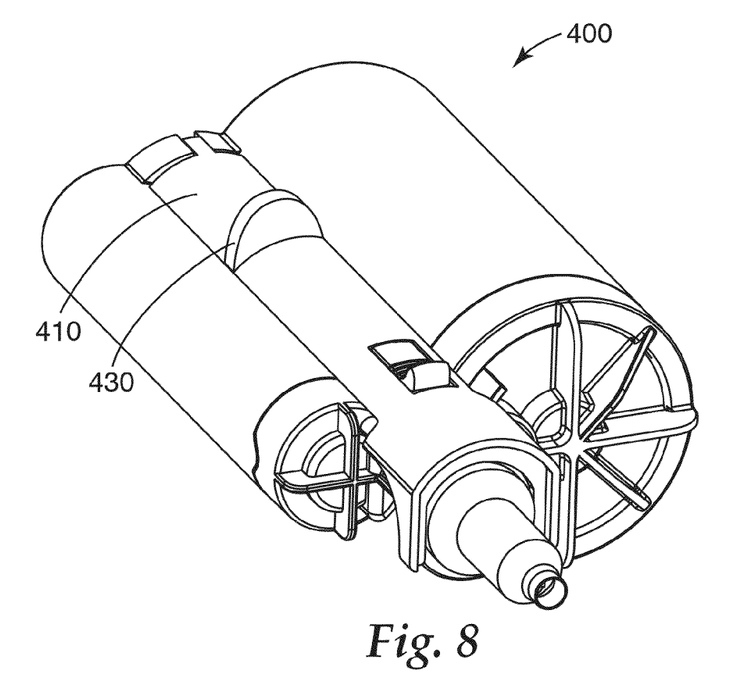
FIG. 8 is a front perspective view of a dispensing cartridge according to a further embodiment of the invention with the locking member in its engaged position.

According to the embodiment shown in FIG. 8, rib 430 extending from the first portion 420 of locking member 410 extends perpendicular to the longitudinal axis of the locking member.

Figure 9:
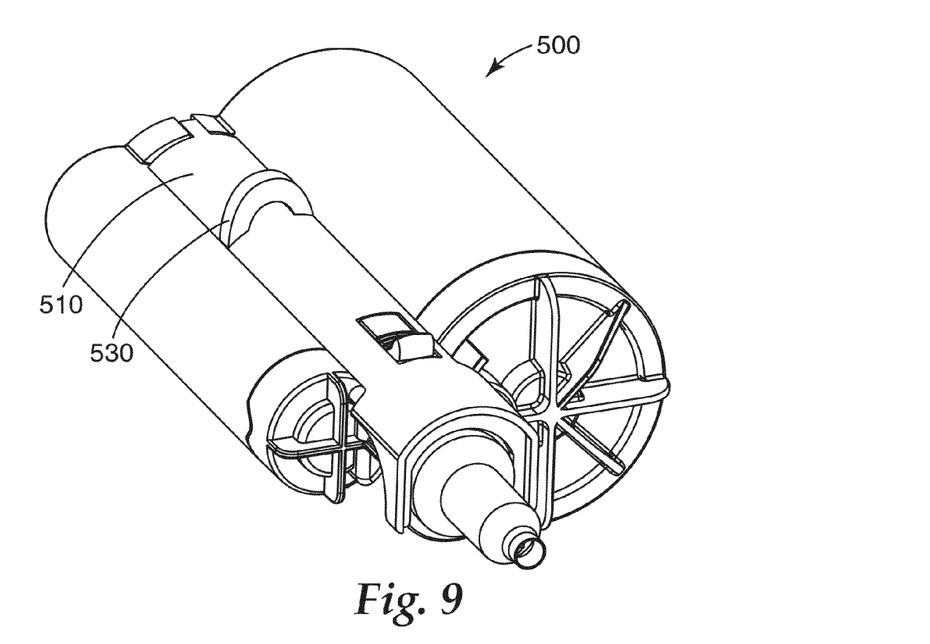
FIG. 9 is a front perspective view of a dispensing cartridge according to a further embodiment of the invention with the locking member in its engaged position.

An alternative of the embodiment of FIG. 8 is shown in FIG. 9. Here, the upstanding rib is provided in the form of an inverse U so that a channel or through hole is formed between the surface of the locking member 510 and the U formed by the rib 530. This permits a user to insert a finger or tool into the through-hole to assist in removing the cartridge.

Figure 10:
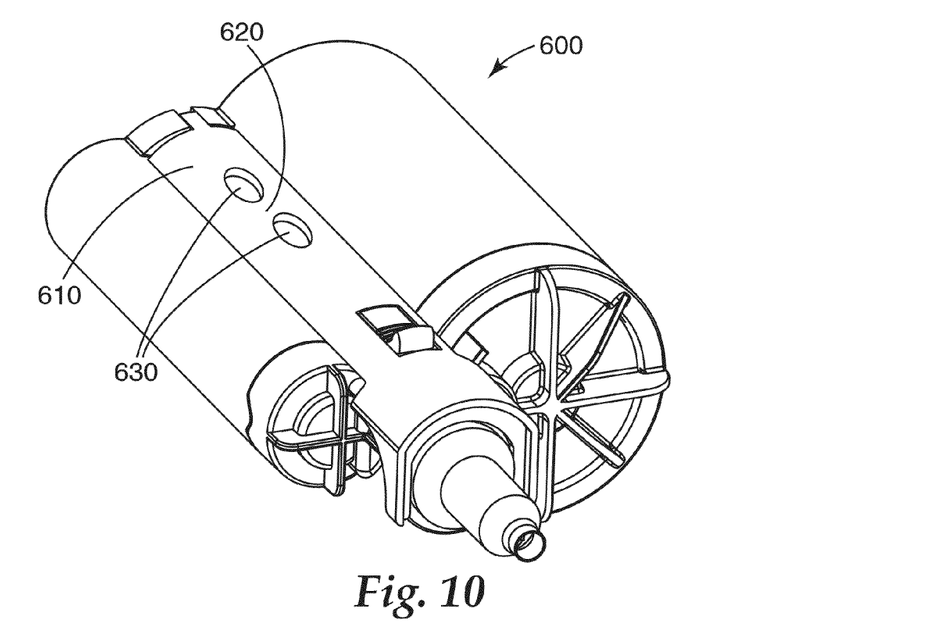
FIG. 10 is a front perspective view of a dispensing cartridge according to a further embodiment of the invention with the locking member in its engaged position.

FIG. 10 shows a further embodiment of the invention. According to this embodiment, locking member 610 comprises a first portion 620 with one or more through holes 630. In FIG. 10, two through holes 630 are shown that are arranged along the longitudinal axis of the locking member 610. The through holes are sized such that a user can insert his/her fingers through the hole to grasp the dispensing cartridge via the locking member 610.

Figure 11:
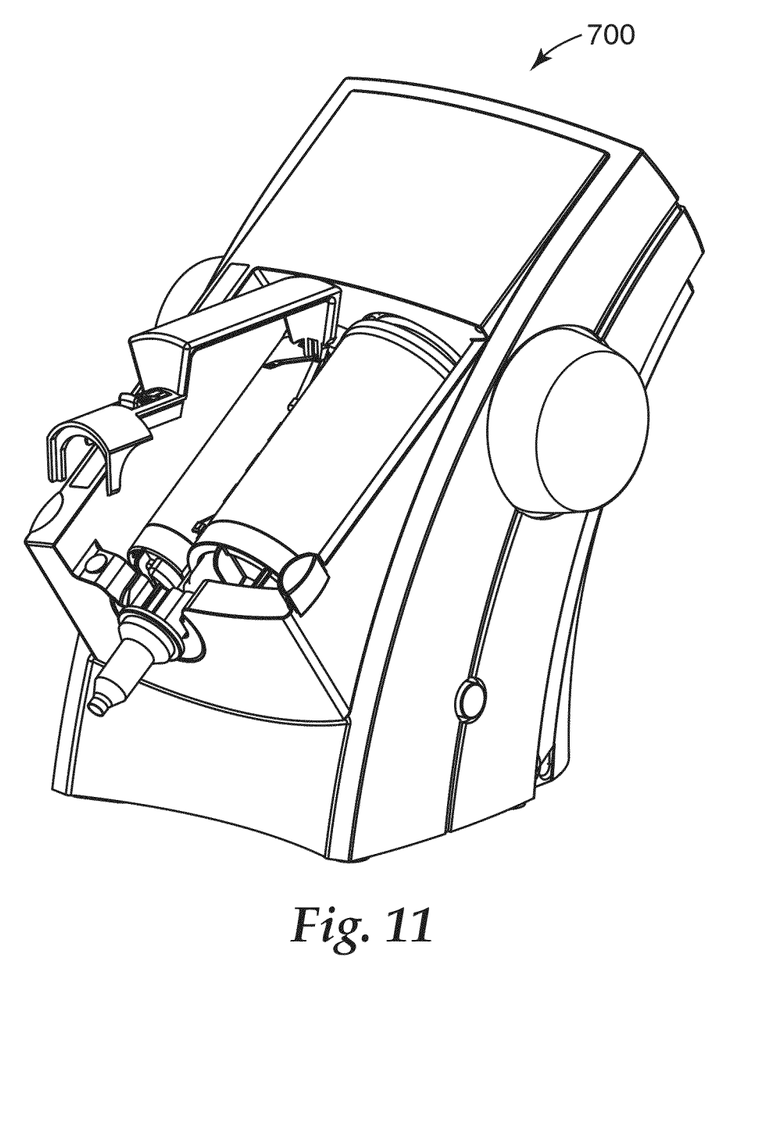
FIG. 11 is a perspective view of the dispensing device with the cartridge of one embodiment the invention placed in the respective accommodating space.

FIG. 11 shows a dispensing device 700. The dispensing cartridge of the embodiment shown in FIGS. 3 and 4 is accommodated in the dispensing device. The locking member is open so that the mixing tip is not yet locked onto the cartridge.

The present invention has now been described with reference to several embodiments thereof. It will be apparent to those skilled in the art that many changes can be made in the embodiments described without departing from the scope of the present invention. Thus the scope of the present invention should not be limited to the structures described in this application, but only by structures described by the language of the claims and the equivalents of those structures.

The invention claimed is:

1. A dispensing cartridge, particularly for dental impression materials, comprising a locking member for locking a tip to at least one of the dispensing cartridge and a container accommodated in the dispensing cartridge, the locking member having a first end and a second end, the locking member being pivotally connectable with the dispensing cartridge at the first end, and the second end of the locking member being adapted for releasable locking engagement with the tip, wherein the locking member comprises a first portion that provides a handle for the user in the locked position of the locking member, allowing the dispensing cartridge to be inserted into or removed from an applicator unit while the locking member is in locking engagement with the tip, wherein the handle is provided by at least one through hole through the first portion of the locking member.

2. The dispensing cartridge of claim 1, wherein the at least one through hole is sized to receive a finger.

* * * * *